United States Patent [19]

Baba et al.

[11] Patent Number: 5,292,505

[45] Date of Patent: Mar. 8, 1994

[54] SULPHATED VINYL POLYMER IN COMPOSITION FOR TREATING RETROVIRAL INFECTIONS

[75] Inventors: Masanori Baba; Erik D. A. De Clercq, both of Leuven, Belgium; Sándor Görög, Budapest, Hungary; Miklós Lów, Budapest, Hungary; Miklós Nagy, Budapest, Hungary; Sándorné Györgyi, Budapest, Hungary

[73] Assignees: Stichting Rega VZW, Leuven, Belgium; Richter Gedeon Vegyeszeti Gyar RT, Budapest, Hungary

[21] Appl. No.: 821,021

[22] Filed: Jan. 15, 1992

Related U.S. Application Data

[62] Division of Ser. No. 315,413, Feb. 23, 1989, Pat. No. 5,152,978.

[30] Foreign Application Priority Data

Feb. 22, 1989 [NL] Netherlands .................. 8900442

[51] Int. Cl.[5] .............................................. A61K 47/34
[52] U.S. Cl. ............................... 424/78.08; 424/78.17; 514/885
[58] Field of Search ............... 424/78.08, 78.27, 70.77, 424/78.17; 525/61; 514/885

[56] References Cited

U.S. PATENT DOCUMENTS

| 3,466,365 | 9/1969 | Schlesinger | 424/78 |
| 3,702,843 | 11/1972 | Schweiger | 525/61 |
| 4,762,715 | 8/1988 | Lukas et al. | 514/934 |

FOREIGN PATENT DOCUMENTS 0093489 3/1986 European Pat. Off. ....... C08F 2/20

OTHER PUBLICATIONS

J. Pol. Sci. (Mar. 1971) Wiley et al.
"New Selective Antiviral Agents Active Against The AIDS Virus" Trends in Pharmacological Sci., vol. 8, No. 9, pp. 339-345 (1987).
"Chemotherapeutic Approach of AIDS" by E. De Clercq, presented at the general meeting of the Academy (1987).
Fischl et al., "The efficacy of Azidothymidine (AZT) in the Treatment of Patients with AIDS and AIDs-Related Complex"New England Journal of Medicine, 317:185-191 (1987).
Mitsuya et al., "Dextran Sulfate Suppression of Viruses in the HIV Family: Inhibition of Virion Binding to CD4± Cells," Science, vol. 240, pp. 646-649 (1988).
Ito et al., "Inhibitory effect of dextran sulfate and heparin on the replication of human immunodeficiency virus (HIV) in vitro," Antiviral Research, 7, 361-3617 (1987).
"Dextran Sulphate, A Potent Anti HIV Agent In Vitro Having Synergism With Zidovudine," The Lancet, p. 1379 (1987).
Baba et al. "Mechanism of inhibitory effect of dextran sulfate and heparin on replication of human immunodeficiency virus in vitro," Proc. Natl. Acad. Sci., vol. 85, pp. 6132-6136 (1988).
Baba et al., "Pentosan polysulfate, a sulfated oligosaccharide, is a potent and selective anti-HIV agent in nitro," Antiviral Research, 9, 335-343 (1988).

(List continued on next page.)

Primary Examiner—Thurman K. Page
Assistant Examiner—Peter F. Kulkosky
Attorney, Agent, or Firm—Webb, Burden, Ziesenheim & Webb

[57] ABSTRACT

Sulphated vinyl polymers such as sulphated polyvinylalcohol, sulphated copolymers of (meth)acrylic acid and vinylalcohol, and pharmaceutically acceptable salts thereof, have an antiviral effect against human immunodeficiency virus and may therefore be used as a therapeutic agent for treating retrovirus infections like AIDS and AIDS-related diseases. Their antiviral activity is apparently based on inhibition of virus adsorption; their inhibitory effect on giant cell formation is stronger than that of dextran sulphate.

7 Claims, 3 Drawing Sheets

OTHER PUBLICATIONS

Nakashima et al., "Effect of 3'-Azido-2',3'-dideoxy-thymidine (AZT) and Neutralizing Antibody on Human Immunodeficiency Virus (HIV-Induced Cytopathic Effects: Implication of Giant Cell Formation for the Spread of virus in Vivo," Virology, 159, 169-173 (1987).

Chargaff et al., "Studies on the Chemistry of Blood Coagulation", Department of Biological Chemistry and Surgery, College of Physicians and Surgeons, Columbia University (1936).

Hallinan et al., "Inhibition of Reverse Transcriptase By Polyvinyl Sulfate (PVS)", Cancer Biochem, Biophys, vo9l. 5, pp. 97-101 (1981).

Chemical Abstracts "Antiviral activity of some synthetic polymers and prospects for their use in practical medicine."

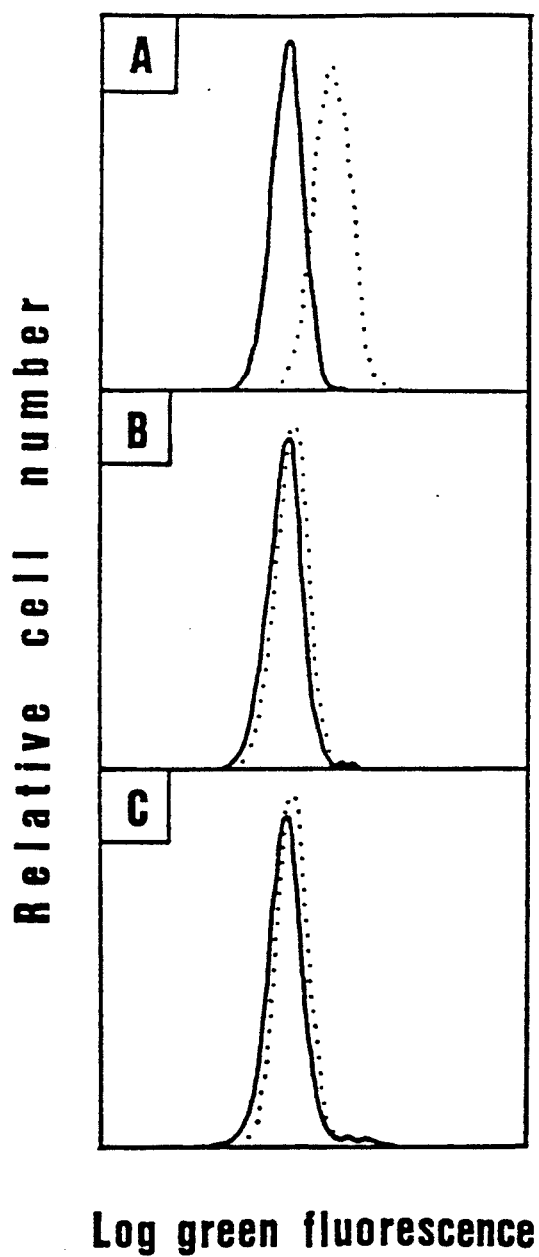

SULPHATED VINYL POLYMER IN COMPOSITION FOR TREATING RETROVIRAL INFECTIONS

This application is a division of application Ser. No. 07/315,413, filed Feb. 23, 1989, now U.S. Pat. No. 5,152,978.

This invention relates to a novel therapeutic agent for treating retroviral infections such as AIDS and AIDS-related diseases.

AIDS or acquired immune deficiency syndrome is a pandemic immunosuppressive disease resulting from the depletion of helper T-lymphocyte cells in the human body. The causative agent has been identified as a retrovirus called "human immunodeficiency virus" or HIV. At the moment, two different types (HIV-1 and HIV-2) of that retrovirus have been described; both types can induce AIDS or AIDS-related diseases although HIV-1 is more widely spread than HIV-2.

Many attempts have already been made to find suitable anti-HIV agents and various substances and compounds have been reported to inhibit the replication of HIV (usually type 1) in vitro.

Among the suggested anti-HIV compounds, 3'-azido-2',3'-dideoxythymidine (azidothymidine or AZT) is at the moment the only compound that has proved to be clinically effective in the treatment of AIDS patients, compare Fischl et al, *New Engl.J.Med.* 317, 185–191 (1987). The activity of AZT (after conversion to its 5'-triphosphate form) is apparently based on inhibition of reverse transcriptase, an enzyme playing a part in the replication of HIV-1 in T-lymphocyte cells.

Further, sulphated polysaccharides such as dextran sulphate, heparin and pentosan polysulphate, are highly potent and selective inhibitors of HIV-1 replication during tests in vitro. Compare:

Ito et al, *Antiviral Res.* 7, 361–367 (1987),

Baba et al, *Proc.Nat.Acad.Sci.USA*, 85, 6132–6136 (1988) and

Baba et al, *Antiviral Res.* 9, 335–343 (1988).

The activity of these sulphated polysaccharides is apparently based on inhibition of the adsorption of virus particles onto the cell membranes of T-lymphocyte cells.

In addition to this known matter, there is need for other substances and compounds acting as potent HIV-inhibitors. Therefore, the invention has for its primary object to provide such inhibitors as well as therapeutic compositions containing the same.

In accordance with the invention, it has now been found that sulphated vinyl polymers such as sulphated polyvinylalcohol and sulphated copolymers of (meth)acrylic acid with vinylalcohol as well as pharmaceutically acceptable salts thereof, are highly potent and selective inhibitors of both HIV-1 and HIV-2 replication in vitro and that they may therefore be used with advantage in pharmaceutical compositions intended for the treatment of retroviral infections such as AIDS and AIDS-related diseases.

The term "sulphated polyvinylalcohol" as used herein refers to a group of polymers of varying molecular weight and polymerisation degree, which have a good solubility in aqueous fluids and which are chemically characterized by the presence of a plurality of —OSO$_3$H groups together with some —OH groups pending from a normal hydrocarbon (polyvinyl) backbone. They can be synthesized by polymerising vinyl acetate or any other hydroxyl-protected vinylalcohol derivative followed by deprotection of the hydroxyl groups in the resulting polymer and by sulphation of the free hydroxyl groups. The sulphation degree can have any value between 50% and 100%.

The sulfated polyvinylalcohol polymers described in the previous paragraph are represented by the following chemical formula:

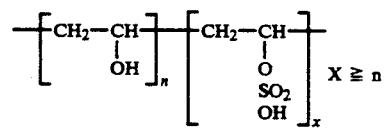

The term "sulphated copolymers of (meth)acrylic acid with vinylalcohol" as used herein refers to a group of polymers of varying molecular weight and polymerisation degree, which have a fair solubility in aqueous fluids and which are chemically characterized by the presence of a plurality of —OSO$_3$H groups together with some free —OH groups as well as —COOH groups and optionally methyl groups pending from a normal (polyvinyl) hydrocarbon backbone. They can be synthesized by copolymerising acrylic or methacrylic acid or reactive derivatives thereof with a hydroxyl-protected vinylalcohol derivative, followed by deprotection of the hydroxyl groups and, if necessary, the carboxyl groups in the resulting copolymer and by sulphation of the free hydroxyl groups. Again the sulphation degree may have any value between 50% and 100%.

The sulfated copolymers of (meth)acrylic acid with vinylalcohol as described in the previous paragraph are represented by the following chemical formula:

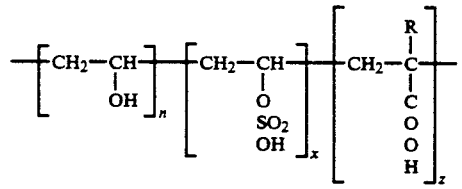

x ≧ n
R = H, CH$_3$

The —OSO$_3$H groups and —COOH groups (if present) may sometimes exist in the form of pharmaceutically acceptable salts; such salts can also be used in the present invention.

The term "sulphated vinyl polymers" is used in this specification to denote the whole group consisting of sulphated of polyvinylalcohols, sulphated copolymers of (meth)acrylic acid and vinylalcohol and pharmaceutically acceptable salts thereof.

It should be noted that such sulphated vinyl polymers differ from sulphated polysaccharides by the fact that they are substantially free of cyclic groups in the hydrocarbon backbones of their molecules.

The sulphated vinyl polymers are known compounds. Sulphated polyvinylalcohols have been disclosed by Chargaff et al in *J.Biol.Chem.* 115, 160 (1936) and are commercially available. Sulphated copolymers of (meth)acrylic acid and vinylalcohol and their salts have been disclosed in EP-A-0093489 where they are intended for use as anticoagulants.

In tests leading to the invention, it was found that the sulphated vinyl polymers completely inhibited the cytopathogenicity of HIV-1 in MT-4 cells and the antigen expression of HIV-1 in CEM cells, at a concentration of 0.8 µg/ml. They were about equally active against HIV-2 replication. This is an important fact because the cytopathogenicity of HIV resulting from its replication in T-cells is normally regarded as the major mechanism for destruction of such cells.

Moreover, and in contrast with azidothymidine, the sulphated vinyl polymers completely inhibited the HIV-1 induced formation of giant cells (multinucleated syncytium cells) from uninfected T-cells, at a concentration of 4 µg/ml. This is important because giant cell formation resulting from the interaction between the gp120 surface antigens of the HIV-infected cells and the CD4 receptor of the uninfected cells is another possible mechanism for the destruction of the T-cells.

Thanks to the inhibition of giant cell formation, the sulphated vinylpolymers of the present invention have a clear advantage over azidothymidine which does not show such effect.

Further, the sulphated vinyl polymers of the invention were found to completely inhibit the adsorption of HIV-particles to CD4 positive cells, at a concentration of about 4 µg/ml. This may account for the strong activity of these polymers against HIV replication.

When the sulphated vinyl polymers of the invention are compared with sulphated polysaccharides such as dextran sulphate, it appears that both groups of compounds have the capability of inhibiting HIV replication, inhibiting giant cell formation and inhibiting virus adsorption to T-cells. Nevertheless, there is a clear difference in activity between these two groups of compounds.

In comparative tests on the inhibition of giant cell formation, it was found that dextran sulphate could completely suppress the giant cell formation only at a concentration of 100 µg/ml. Such a concentration is extremely high and hardly achievable in human plasma.

On the other hand, the sulphated vinyl polymers of the present invention were capable of completely blocking the giant cell formation at a concentration of 4 ug/ml, which concentration can be readily achieved.

Thus, the sulphated vinyl polymers have a clear advantage over sulphated polysaccharides like dextran sulphate.

Therapeutic compositions, containing the sulphated vinyl polymers of the invention as an active ingredient for the treatment of retroviral infections such as AIDS or AIDS-related diseases in human practice may take the form of powders, suspensions, solutions, sprays, emulsions, unguents or creams and may be used for local application, for intranasal, rectal, vaginal and also for oral or parenteral (intravenous, intradermal, intramuscular, intrathecal etc.) administration. Such compositions may be prepared by combining (e.g. mixing, dissolving etc.) the sulphated vinyl polymers with pharmaceutically acceptable excipients of neutral character (such as aqueous or non-aqueous solvents, stabilizers, emulsifiers, detergents, additives) and further, if necessary with dyes and aromatizers. The concentration of the active ingredient in the therapeutic composition may vary widely between 0.1% and 100%, depending on the mode of administration. Further, the dose of the active ingredient to be administered may vary between 0.1 mg and 100 mg/kg of body weight.

The anti-HIV properties of the sulphated vinyl polymers are documented by the following examples which should not be read in a restricting sense. Dextran sulphate is used for comparison therein.

In the Examples, reference is made to FIGS. 1-3 of the attached drawing, wherein:

FIG. 3 is a graphical representation of the results of tests on the inhibition of HIV-adsorption.

Figure 1:
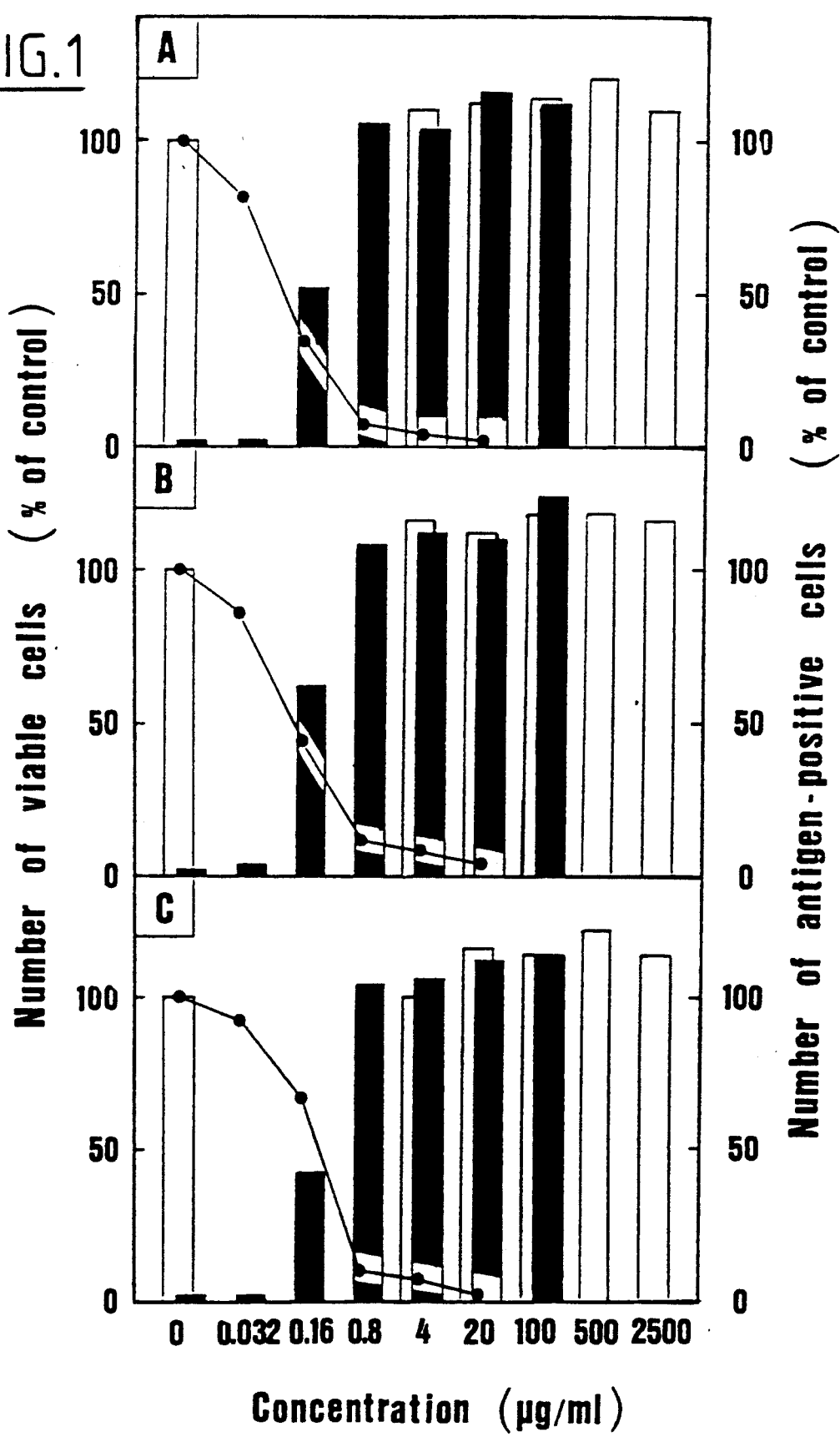
FIG. 1 is a diagrammatic representation of the results of tests on the inhibition of cytopathogenicity of HIV-1 together with test results on the inhibition of virus antigen expression.

The viruses used in the examples were HIV-1 and HIV-2. They were obtained from the culture supernatant of HUT-78 cells persistently infected with HIV-1 and from the culture supernatant of CEM cells persistently infected with HIV-2, respectively. Titers of HIV-1 and HIV-2 stocks were $2 \times 10^5$ and $5 \times 10^4$ CCID$_{50}$ (one CCID$_{50}$ being the 50% cell culture infective dose) per ml, respectively.

The cells used in the Examples were MT-4, CEM and Molt-4 (clone No. 8) cells. The MT-4 cells, disclosed by I. Miyoshi et al., *Gann Monogr.* 28, 219–228 (1982) were used for tests on the inhibition of the cytopathogenicity of HIV and tests on the inhibition of virus adsorption. The CEM cells, disclosed by Foley et al., *Cancer*, 18, 522–529, (1965), were used for tests about the inhibition of viral antigen expression, whereas Molt-4 (clone No. 8) cells, disclosed by Kikukawa et al., *J. Virol.* 57, 1159–1162 (1986) were used in the giant cell formation assay. All cells were mycoplasmanegative. The cells were grown and maintained in a culture medium consisting of RPMI 1640 medium supplemented with 10% heat-inactivated fetal calf serum, 100 U/ml penicillin G and 20 µg/ml gentamicin. This RPMI 1640 medium is a standard medium comprising inorganic salts like NaCl, NaHCO$_3$, Na$_2$HPO$_4$ etc. as well as glucose, several amino acids and several vitamins.

Four different substances were used as test compounds, namely:

PAVAS (MW 10,000), a sulphated copolymer of acrylic acid and vinylalcohol (monomer ratio 1:9) having a molecular weight of 10,000 and a sulphation degree of 60%;

PAVAS (MW 20,000), a sulphated copolymer of acrylic acid and vinylalcohol (monomer ratio 1:9) having a molecular weight of 20,000 and a sulphation degree of 50%;

PVAS (MW 20,000), a sulphated polyvinylalcohol of molecular weight 20,000 and a sulphation degree of 50%;

Dextran sulphate (MW 5,000), a sulphated dextran having a molecular weight of 5,000 and a sulphation degree of about 67%.

EXAMPLE 1

Inhibition of Cytopathogenicity of HIV-1.

The test compounds were evaluated for their inhibitory effect on the cytopathogenicity of HIV-1 in MT-4 cells. The method has been described by R. Pauwels et al. in *J.Virol.Methods*, 16, 171–185, (1987).

In a first series of tests, MT-4 cells were suspended in culture medium at $3 \times 10^5$ cells/ml and infected with HIV-1 at 1,000 CCID$_{50}$/ml. Immediately after infection, 100 µl portions of the cell suspension were placed into the wells of a microtiter ® tray containing various concentrations of the test compounds. After 5 days incubation at 37° C., the number of viable cells in each well was determined by means of a colorimetric assay (MTT method), using 3-(4,5-dimethylthiazol-2-yl)-2,5-diphenyltetrazolium bromide as a colorant. This colorimetric assay has been described by Pauwels et al in *J.Virol.Methods*, 20, 309–321 (1988).

A second series of tests, parallel to the first, was effected with mock-infected cells, incubated in the presence of various concentrations of the test compounds. A control test was effected by incubating mock-infected cells in the absence of any test compound.

The results of these tests are represented by the bar diagrams of FIG. 1, obtained by plotting the number of viable cells after 5 days incubation (in percent of the number in the control test) against the concentration of the test compound in each test. Black bars refer to tests with virus-infected cells and white bars refer to tests with mock-infected cells. Panels A,B and C relate to tests with PAVAS (MW 10,000), PAVAS (MW 20,000) and PVAS (MW 20,000) respectively.

It can be deduced from FIG. 1 that all three test compounds completely protected the cells against virus-induced cell destruction at a concentration of 0.8 ug/ml.

None of the three test compounds reduced the viability of mock-infected MT-4 cells at concentrations up to 2500 μg/ml. Thus, the 50% cytotoxic dose ($CD_{50}$) of the compounds for MT-4 cells was higher than 2500 μg/ml.

EXAMPLE 2

Inhibition of Viral Antigen Expression

The test compounds were also evaluated for their inhibitory effect on the expression of viral antigens in HIV-infected CEM cells. Here, CEM cells were suspended in the culture medium at $1 \times 10^5$ cells/ml and infected with HIV-1 at a multiplicity of infection of 0.04. The infected cells were incubated in the presence of various concentrations of the test compound. After 4 days incubation, the viral antigen expression was measured by indirect immunofluorescence and laser cytofluorography, using polyclonal antibody as a probe.

The method has been described by Pauwels et al. in *J.Virol.Methods*, 16, 171–185 (1987).

A control test was effected in the absence of any test compound.

The results of these tests have been indicated in FIGS. 1A, 1B and 1C by means of curves (●–●) obtained by plotting the number of antigen positive cells (in percent of the number of untreated virus-infected cells) against the concentration of the test compound in each test. Again, FIGS. 1A, 1B and 1C relate to tests with PAVAS (MW 10,000), PAVAS (MW 20,000) and PVAS (MW 20,000), respectively.

It appears from the curves in FIGS. 1A, 1B and 1C that the three test compounds almost completely inhibited the viral antigen expression of HIV-1 in CEM cells at a concentration of 0.8 μg/ml and higher.

During a parallel series of tests, it appeared that none of the test compounds reduced the viability of mock-infected CEM cells at concentrations up to 500 ug/ml. Thus, the cytotoxic dose ($CD_{50}$) of the test compounds for CEM cells was higher than 500 ug/ml.

EXAMPLE 3

Inhibition of HIV-Induced Cytopathogenicity and of HIV Antigen Expression

The tests of Examples 1 and 2 were expanded to cover both HIV-1 and HIV-2 as test viruses and both MT-4 and CEM cells as test cells. Further, PAVAS (MW 10,000), PAVAS (MW 20,000), PVAS (MW 20,000) as well as Dextran sulphate (MW 5,000) were used as test compounds.

The results, expressed in values for $ED_{50}$ (the 50% antivirally effective dose) and $CD_{50}$ (the 50% cytotoxic dose) are shown in Table 1 where all data are mean values of two separate experiments.

TABLE 1

| Compound | Cell | $ED_{50}$ (μg/ml) HIV-1 | $ED_{50}$ (μg/ml) HIV-2 | $CD_{50}$ (μg/ml) |
|---|---|---|---|---|
| PAVAS (MW: 10,000) | MT-4 | 0.15 | 0.29 | >2500 |
|  | CEM | 0.10 | 0.14 | >500 |
| PAVAS (MW: 20,000) | MT-4 | 0.11 | 0.31 | >2500 |
|  | CEM | 0.14 | 0.19 | >500 |
| PVAS (MW: 20,000) | MT-4 | 0.18 | 0.28 | >2500 |
|  | CEM | 0.23 | 0.39 | >500 |
| Dextran sulphate (MW: 5,000) | MT-4 | 0.39 | 0.07 | >2500 |
|  | CEM | 1.40 | 0.12 | >500 |

It can be deduced from Table 1 that the antivirally effective doses of all four test compounds are far below the cytotoxic doses thereof. Further, it can be seen that PAVAS and PVAS are equally inhibitory to HIV-2 and HIV-1 replication in both MT-4 and CEM cells. PAVAS and PVAS are slightly more active than dextran sulphate against HIV-1 and slightly less active than dextran sulphate against HIV-2.

EXAMPLE 4

Inhibition of Giant Cell Formation

Molt-4 cells were co-cultured with an equal number ($5 \times 10^4$) of HIV-1-infected HUT-78 cells in the wells of a microtiter ® tray containing various concentrations of the test compounds. After 24 hours of incubation, the cell clusters were broken by gentle pipetting and the number of giant cells (multinucleated syncytial cells) was recorded microscopically. A control test was effected in the absence of any test compound.

The control test revealed the formation of giant cells. Such giant cells were not observed when the Molt-4 cells had been co-cultured with uninfected HUT-78 cells.

Figure 2:
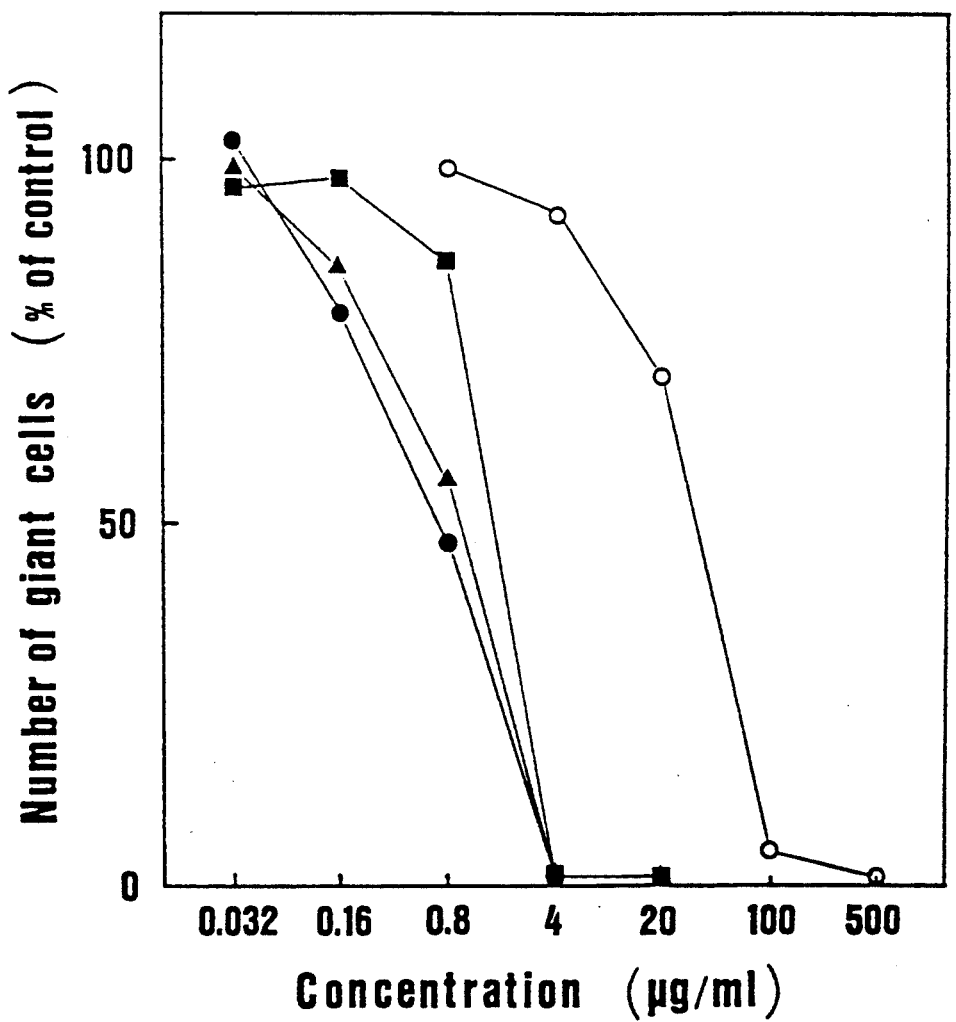
FIG. 2 is a graphical representation of the results of tests on the inhibition of giant cell formation.

The results of the tests with various concentrations of the test compounds are graphically represented in FIG. 2 where the number of giant cells after 24 hours incubation (in percent of the number in the control test) has been plotted against the concentration of the test compound in each test.

The curves in FIG. 2 can be identified as follows:
●–● PAVAS (MW 10,000)
△ - △ PAVAS (MW 20,000)
■ - ■ PVAS (MW 20,000)
○–○ Dextran sulphate (MW 5,000)

It appears from FIG. 2 that giant cell formation could be completely inhibited by PAVAS and PVAS at concentrations of 4 ug/ml. Even at a lower concentration of 0.8 μg/ml, PAVAS (MW 10,000) and PAVAS (MW 20,000) achieved a reduction of approximately 50% in the number of giant cells.

On the other hand, and in marked contrast thereto, dextran sulphate was not inhibitory to giant cell formation at a concentration of 4 μg/ml. This dextran sulphate required a concentration of 100 ug/ml to completely suppress giant cell formation.

In another series of experiments, PAVAS (MW 10,000) and PAVAS (MW 20,000) and PVAS (MW 20,000) also inhibited the giant cell formation induced by HIV-2, at concentrations similar to those required for inhibition of giant cell formation induced by HIV-1.

Thus, PAVAS and PVAS are potent inhibitors of giant cell formation induced by HIV-1 and HIV-2.

EXAMPLE 5

Inhibition of Virus Adsorption

The inhibitory effect of the test compounds on virus adsorption was measured by an indirect immunofluorescence/laser flow cytographic method which had been established for this purpose.

In this test, MT-4 cells were exposed to HIV-1 virions which had been concentrated from the supernatant of HIV-1-infected HUT-78 cells, in the presence or absence of test compounds. After 30 minutes incubation at 37° C., the cells were thoroughly washed with phosphate-buffered saline (at 4° C.) to remove unadsorbed virus particles. Then, the cells were processed for indirect immunofluorescence using polyclonal antibody to HIV-1 and analysed for cell-bound HIV-1 virions by laser flow cytofluorography. A control test was effected with MT-4 cells without exposing them to HIV-1 virions.

The results are represented in the fluorescence histograms of FIG. 3 which have been obtained by plotting the relative cell number belonging to a certain intensity of green fluorescence against the logarithm of that intensity.

Solid-line histograms represent the fluorescence of MT-4 cells in the control tests, while dotted-line histograms represent the fluorescence of MT-4 cells in the actual tests. Panels A,B and C refer to tests without any test compound, to tests with dextran sulphate (MW 5,000) at 20 μg/ml, and to tests with PAVAS (MW 20,000) at 4 μg/ml, respectively.

It can be noted from panel A that, in the absence of any test compound, there is a clear difference in fluorescence properties between MT-4 cells exposed to HIV-1 virions and MT-4 cells not exposed thereto. In fact, exposure to HIV-1 virions results in a shift of the histogram to higher fluorescence intensities.

Panel B shows that, if the tests are carried out in the presence of 20 μg/ml dextran sulphate, both histograms will coincide, meaning that there is no difference anymore between the fluorescence properties of MT-4 cells exposed or not exposed to HIV-1 virions. This means that the binding of HIV-1 virions to MT-4 cells is completely blocked by 20 μg/ml of dextran sulphate.

In the same way, panel C shows that virus adsorption onto the MT-4 cells can be suppressed completely by 4 μg/ml of PAVAS (MW 20,000).

The same results could be achieved with PAVAS (MW 10,000) and with PVAS (MW 20,000) (data not shown).

What we claim is:

1. A pharmaceutical composition in unit dosage form for treating of immunodeficiency disease causally connected to human immunodeficiency virus, comprising at least one pharmaceutically acceptable excipient and a quantity of a sulfated vinyl polymer active ingredient selected from the group consisting of sulfated polyvinylalcohol and sulfated copolymers of (meth)acrylic acid and vinylalcohol, wherein said sulfated vinyl polymer further has a sulfation degree between 50 and 60%, in an amount which upon administration of one or more unit doses thereof establishes a blood plasma concentration of 0.8–4 μg/ml, effective to treat said immunodeficiency disease, and to demonstrate improved effectiveness against HIV-1 and HIV-2 virus, in a patient to which one or more unit doses are administered.

2. The pharmaceutical composition according to claim 1 wherein said active ingredient is a sulfated copolymer of acrylic acid and vinylalcohol in a monomer ratio of about 1:9.

3. The pharmaceutical composition according to claim 2 wherein said sulfated copolymer has a molecular weight of about 10,000 and a sulfation degree of about 60%.

4. The pharmaceutical composition according to claim 2 wherein said sulfated copolymer has a molecular weight of about 20,000 and a sulfation degree of about 50%.

5. The pharmaceutical composition according to claim 1 wherein said active ingredient is a sulfated polyvinylalcohol having a molecular weight of about 20,000 and a sulfation degree of about 50%.

6. The pharmaceutical composition as set forth in any one of claims 1–5, wherein said active ingredient is present in a concentration of 0.1 to 100%.

7. The pharmaceutical composition as set forth in any one of claims 3–5, wherein said pharmaceutical composition has the form of a powder, suspension, solution, spray, emulsion, unguent or cream.

* * * * *

UNITED STATES PATENT AND TRADEMARK OFFICE
CERTIFICATE OF CORRECTION

PATENT NO. : 5,292,505  
DATED : March 8, 1994  
INVENTOR(S) : Masanori Baba et al.

Page 1 of 2

It is certified that error appears in the above-indentified patent and that said Letters Patent is hereby corrected as shown below:

Title page, after [54], "POLYMER" and "COMPOSITION" should read --POLYMERS-- and --COMPOSITIONS--, respectively.

Title page, under References Cited, OTHER PUBLICATIONS, "Baba et al., "Pentosan polysulfate, a sulfated oligosaccharide, is a potent and selective anti-HIV agent in nitro," Antiviral Research, 9, 335-343 (1988)." should read --Baba et al., "Pentosan polysulfate, a sulfated oligosaccharide, is a potent and selective anti-HIV agent in vitro," Antiviral Research, 9, 335-343 (1988).--.

Title page, under References Cited, OTHER PUBLICATIONS, page 2, "Hallinan et al., "Inhibition of Reverse Transcriptase By Polyvinyl Sulfate (PVS)", Cancer Biochem, Biophys, vo91. 5, pp. 97-101 (1981)." should read --Hallinan et al., "Inhibition of Reverse Transcriptase By Polyvinyl Sulfate (PVS)", Cancer Biochem, Biophys, vol. 5, pp. 97-101 (1981).--.

Column 2 Line 55 after "sulphated" delete "of".

Column 3 Line 45 "ug/ml" should read --$\mu$g/ml--.

UNITED STATES PATENT AND TRADEMARK OFFICE
CERTIFICATE OF CORRECTION

PATENT NO. : 5,292,505
DATED : March 8, 1994
INVENTOR(S) : Masanori Baba et al.

It is certified that error appears in the above-indentified patent and that said Letters Patent is hereby corrected as shown below:

Col. 4, Line 6 "drawing" should read --drawings--.

Column 4 Line 36 "100 U/ml" should read --100 µg/ml--.

Column 5 Line 27 "ug/ml." should read -- µ g/ml.--.

Column 5 Line 66 "ug/ml." should read -- µ g/ml.--.

Column 5 Line 68 "ug/ml." should read -- µg/ml.--.

Column 6 Line 65 "ug/ml." should read -- µg/ml.--.

Column 7 Line 4 "ug/ml" should read --µ g/ml--.

Column 7 Line 40 "A,3" should read --A, B--.

Claim 1 Line 14 Column 8 "disease" should read --diseases--.

Claim 2 Line 31 Column 8 after "1:9" insert --said copolymer having a sulfation degree between 50 and 60%--.

Signed and Sealed this

Sixteenth Day of August, 1994

Attest:

Attesting Officer

BRUCE LEHMAN

Commissioner of Patents and Trademarks